US008329184B2

(12) United States Patent
Biemans et al.

(10) Patent No.: US 8,329,184 B2
(45) Date of Patent: Dec. 11, 2012

(54) PROCESS FOR MANUFACTURING VACCINES

(75) Inventors: Ralph Leon Biemans, Rixensart (BE); Pierre Duvivier, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 749 days.

(21) Appl. No.: 11/917,580

(22) PCT Filed: Jun. 23, 2006

(86) PCT No.: PCT/EP2006/006270
§ 371 (c)(1),
(2), (4) Date: Dec. 14, 2007

(87) PCT Pub. No.: WO2007/000343
PCT Pub. Date: Jan. 4, 2007

(65) Prior Publication Data
US 2010/0215686 A1   Aug. 26, 2010

(30) Foreign Application Priority Data

| Jun. 27, 2005 | (GB) | 0513069.5 |
| Jun. 27, 2005 | (GB) | 0513071.1 |
| Jul. 28, 2005 | (GB) | 0515556.9 |
| Nov. 28, 2005 | (GB) | 0524204.5 |
| Dec. 21, 2005 | (GB) | 0526040.1 |
| Dec. 21, 2005 | (GB) | 0526041.9 |

(51) Int. Cl.
A61K 39/00 (2006.01)
A61K 39/02 (2006.01)
A61K 39/385 (2006.01)
C12P 19/00 (2006.01)

(52) U.S. Cl. ............... 424/184.1; 424/193.1; 424/234.1; 435/72

(58) Field of Classification Search ........................ None
See application file for complete search history.

(56) References Cited

U.S. PATENT DOCUMENTS

| 4,365,170 A | 12/1982 | Okuhara |
| 4,376,760 A | 3/1983 | Jung et al. |
| 4,673,574 A | 6/1987 | Anderson et al. |
| 5,180,815 A | 1/1993 | Masuda |

FOREIGN PATENT DOCUMENTS

| EP | 0 161 188 | 11/1985 |
| EP | 0 208 375 | 1/1987 |
| EP | 0 471 177 | 2/1990 |
| EP | 0 378 881 | 7/1990 |
| EP | 0 427 347 | 5/1991 |
| EP | 0 497 525 | 12/1991 |
| EP | 0 477 508 | 1/1992 |
| WO | 91/01146 | 7/1990 |
| WO | 93/15760 | 2/1993 |
| WO | 93/17712 | 9/1993 |
| WO | 94/03208 | 2/1994 |
| WO | 95/08348 | 3/1995 |
| WO | 96/29094 | 9/1996 |
| WO | 96/40242 | 12/1996 |
| WO | 98/26799 | 6/1998 |
| WO | 98/58668 | 12/1998 |
| WO | 98/85668 | 12/1998 |
| WO | 99/18121 | 4/1999 |
| WO | 99/55715 | 11/1999 |
| WO | 00/56360 | 9/2000 |
| WO | 00/61761 | 10/2000 |
| WO | 01/72337 | 10/2001 |
| WO | 02/91998 | 5/2002 |
| WO | 03007985 | 1/2003 |
| WO | 2004/014417 | 2/2004 |
| WO | 2004/014418 | 2/2004 |
| WO | 2004/014419 | 2/2004 |
| WO | 2007/000341 | 1/2007 |
| WO | 2007/000342 | 1/2007 |
| WO | 20080111201 | 1/2008 |

OTHER PUBLICATIONS

Carmenate Tania, et al, "Effect of conjugation methodology on the immunogenicity and protective efficacy of meningococcal group C polysaccharide-P64k protein conjugates," FEMS Immunology and Medical Microbiology, Elsevier Science B.V., Amsterdam, NL., vol. 40, No. 3, (Apr. 9, 2004), pp. 193-199.

Schneerson et al., Infection and Immunity, Quantitative and Qualitative Analyses of Serum Antibodies Elicited in Adults by Haemophitus influenza Type b and Pneumococcus Type 6A Capsula Polysaccharide-Tetanus Toxoid Conjugates, Infection and Immunity, 52:519-528 (1986).

Dintzis, Rational design of conjugate vaccines; Pediatric Research, 32:376-385 (1992).

Linberg, Glycoprotein conjugate vaccines, Vaccine, 17:S28-S36 (1999).

Constantino P. et al., Development and Phase 1 Clinical Testing of a Conjugate Vaccine against Meningococcus A and C, Vaccine, 10:691-698 (Jan. 1992).

Kossaczka Z et al., American Society for Microbiology, Synthesis and Immunological Properties of VI and Di-Omicron-Acetyl Pectin Protein Conjugates with Adipic Acid Dihydrazide as The Linker, American Society for Microbiology, vol. 65, No. 6, pp. 2088-2093 (Jun. 1997).

Wang J et al., The Bio Chemical Journal, An Active Immunization Approach to Generate Protective Catalytic Antibodies, The Bio Chemical Journal, vol. 360, No. Pt 1, pp. 151-157 (Nov. 15, 2001).

Halsey N A, Clinical Infectious Diseases, Combination Vaccines: Defining and Addressing Current Safety Concerns, 33:(Suppl 4) pp. 312-318, (2001).

Chu, et al., Further Studies on the Immunogenicity of *Haemophilus influenzae* Type b and Pneumonal Type 6A Polysaccharide-Protein Conjugates, Infection and Immunity, 40(1), p. 245-256, 1983.

(Continued)

Primary Examiner — Albert Navarro
(74) Attorney, Agent, or Firm — Eric J. Kron

(57) ABSTRACT

The present application discloses an improved method for conducting saccharide-protein conjugation reactions using carbodiimide condensation chemistry. Depending on the nature of the saccharide or protein carrier involved, the quality of the conjugate may be improved by adding one of the reaction components slowly to the reaction mixture. Immunogenic compositions are further provided comprising the saccharide-protein conjugates made by the methods disclosed.

49 Claims, No Drawings

OTHER PUBLICATIONS

Nakajima and Ikada et al., Mechanism of Amide Formation by Carbodiimide for Bioconjugation in Aqueous Media, Bioconjugate Chem., 6, p. 123-130, 1995.

Hoare and Kohsland, A Method for the Quantitative Modification and Estimation of Carbolxylic Acid Groups in Proteins, The Journal of Biological Chemistry, vol. 242, No. 10, pp. 2447-2453, 1967.

Szu et al., Ultrasonic Irradiation of Bacterial Polysaccharides Characterization of the Depolymerized Products and Some Applications of the Process, Carbohydrate Research, 152 p. 7-20, 1986.

Kuo, et al., Characterization of a Recombinant Pneumolysin and Its Use as a Protein Carrier for Pneumococcal Type 18C Conjugate Vaccines, Infection and Immunity, Vo. 63, No. 7, pp. 2706-2713, Jul. 1995.

Falugi, et al., Rationally Designed Strings of Promiscuous CD4 T cell epitopes provide help to Haemophilus influenzae type B Obligosaccharide; a model for new conjugate vaccines, 31; pp. 3816-3824, 2001.

Pierce, et al., Cross Linking Reagents Technical Handbook, 2005, pp. 1-48.

Wilkinson, et al., Immune Response to a Mucosally Administered Allatoxin B1 Vaccine, Immunology and Molecular Biology, Poultry Science, 82; pp. 1565-1572, 2003.

Kossaczka Z et al., Vibrio Cholerae 0139 Conjugate Vaccines: Synthesis and Immunogenicity of V, cholerae 0139 Capsular Polysaccharide Conjugates with Recombinant Diphtheria Toxin Mutant in Mice, Infection and Immunity, vol. 68, No. 9., pp. 5037-5043, 2000.

Beuvery, et al., Preparation and Immunochemical Characterization of Meningococcal Group C polysaccharide-tetanus Toxoid Conjugates as a new generation of vacines, Infection and Immunity, 40(1) pp. 39-45, 1983.

Gu, et al., Preparation Characterization, and Immunogenicity of meningococcal Lipooligosaccharide-derived Oligosaccharide-protein Conjugates; Infectious and Immunity 61(5) pp. 1873-1880, 1993.

Que, et al., Effect of Carrier selection on Immunogenicity of Protein Conjugate Vaccines against Plasmodium Falciparum Circumsporozoites, Infection and Immunity, 56(10): pp. 2645-2649; 1988.

Jin, et al., Preparation and Characterization of Group A Meningogoccal Capsular Polysaccharide Conjugates and Evlauation of Their Immunogenicity in Mice; Infection and Immunity, 71(9) pp. 5115-5120, 2003.

Bartoloni, et al., Immunogenicity of meningococcal B polysaccharide conjugated to tetanus toxoid or CRM197 via Adipic Acid Dihydrazide, Vaccine, vol. 13, No. 5, pp. 463-470, 1995.

Schneerson, et al., Synthesis of a conjugate Vaccine Composed of Pneumococcus Type 14 Capsular Polysaccharide Bound to Pertussis Toxin, Infection and Immunity, 60(9), pp. 3258-3532, 1992.

Shen, et al., Preparation and Preclinical Evaluation of Experimental Group B Streptococcus Type III polysaccharide-cholera toxin B subunit conjugate Vaccine for Intranasal Immunization., Vaccine, vol. 19, pp. 850-861, 2001.

Schneerson, et al., Preparation, Characterization and Immunogenicity of Haemophilus influenzae Type b Polysaccharide Protein Conjugates, The Journal of Experimental Medicine, vol. 152, pp. 361-376, 1980.

Beuvery et al., Comparison of the Induction of Immunoglobulin M and G antibodies in mice with Purified Pneumococcal Type 3 and Meningococcal Group C Polysaccharides and their Protein Conjugates., Infection and Immunity, vol. 37 (1), p. 15-22, 1982.

Chibber, et al., Protection in a Mouse Peritonitis Model Mediated by Iron-Regulated Outer-Membrane Protein of Salmonella typhi Coupled to its VI antigen., Journal of Medical Microbiology, vol. 53., pp. 705-709, 2004.

Corbel, et al., Control Testing of Combined Vaccines: A Consideration of Potential Problems and Approaches, Biologicals, vol. 22, pp. 353-360, 1994.

Devi, et al., Antibodies to Poly [(2-8)-a-N-acetylneuraminic acid] and poly [(2-9)-a-N-acetylneuraminic acid] are elicited by immunication of mice with Escherichia coli K92 conjugates: Potential Vaccines for groups B and C meningococci and E. coli K1: vol. 88, pp. 7175-7179, Aug. 1991.

PROCESS FOR MANUFACTURING VACCINES

This application is filed pursuant to 35 U.S.C. §371 as a United States National Phase Application of International Patent Application Serial No. PCT/EP2006/006270 filed Jun. 23, 2006, which claims priority from Great Britain Application No. 0513069.5 filed in the United Kingdom on Jun. 27, 2005, Great Britain Application No. 0513071.1 filed in the United Kingdom on Jun. 27, 2005, Great Britain Application No. 0515556.9 filed in the United Kingdom on Jul. 28, 2005, Great Britain Application No. 0524204.5 filed in the United Kingdom on Nov. 28, 2005, Great Britain Application No. 0526040.1 filed in the United Kingdom on Dec. 21, 2005, and Great Britain Application No 0526041.9 filed in the United Kingdom on Dec. 21, 2005, the content of which is incorporated herein by reference.

The present invention relates to improved methods of conducting carbodiimide condensation reactions. In particular, it relates to the conjugation of saccharides and proteins using carbodiimide condensation. It also relates to immunogenic compositions that may be made comprising the saccharide-protein conjugates of the invention.

The use of bacterial capsular polysaccharides has been widely used in immunology for many years for the prevention of bacterial disease. A problem with such a use, however, is the T-independent nature of the immune response. These antigens are thus poorly immunogenic in young children. This problem has been overcome through conjugating the polysaccharide antigens to a protein carrier (a source of T-helper epitopes) which may then by used to elicit a T-dependent immune response, even in the first year of life.

Various conjugation techniques are known in the art. Conjugates can be prepared by direct reductive amination methods as described in U.S. Pat. No. 4,365,170 (Jennings) and U.S. Pat. No. 4,673,574 (Anderson). Other methods are described in EP-O-161-188, EP-208375 and EP-O-477508. The conjugation method may alternatively rely on activation of hydroxyl groups of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the cyanate ester can be coupled with hexane diamine or adipic acid dihydrazide (ADH or AH) and the amino-derivatised saccharide is conjugated to the carrier protein using carbodiimide (e.g. EDAC or EDC) chemistry via a carboxyl group on the protein carrier. Such conjugates are described in PCT published application WO 93/15760 Uniformed Services University and WO 95/08348 and WO 96/29094. See also Chu C. et al Infect. Immunity, 1983 245 256.

In general the following types of chemical groups on a protein carrier can be used for coupling/conjugation:
A) Carboxyl (for instance via aspartic acid or glutamic acid) which may be conjugated to natural or derivatised amino groups on saccharide moieties using carbodiimide chemistry;
B) Amino group (for instance via lysine) which may be conjugated to natural or derivatised carboxyl groups on saccharide moieties using carbodiimide chemistry;
C) Sulphydryl (for instance via cysteine);
D) Hydroxyl group (for instance via tyrosine);
E) Imidazolyl group (for instance via histidine);
F) Guanidyl group (for instance via arginine); and
G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.

Direct Coupling Approaches:
Saccharide-OH+CNBr or CDAP---->cyanate ester+NH2-Prot---->conjugate
Saccharide-aldehyde+NH2-Prot---->Schiff base+NaCNBH3---->conjugate
Saccharide-COOH+NH2-Prot+EDAC---->conjugate
Saccharide-NH2+COOH-Prot+EDAC---->conjugate Indirect Coupling Via Spacer (Linker) Approaches:
Saccharide-OH+CNBr or CDAP---->cyanate ester+NH2----NH2---->saccharide----NH2+COOH-Prot+EDAC----->conjugate
Saccharide-OH+CNBr or CDAP---->cyanate ester+NH2-----SH----->saccharide----SH+SH-Prot (native Protein with an exposed cysteine or obtained after modification of amino groups of the protein by SPDP for instance)----->saccharide-S—S-Prot
Saccharide-OH+CNBr or CDAP--->saccharide----SH+maleimide-Prot (modification of amino groups)---->conjugate
Saccharide-COOH+EDAC+NH2-----NH2--->saccharide------NH2+EDAC+COOH-Prot---->conjugate
Saccharide-COOH+EDAC+NH2----SH---->saccharide----SH+SH-Prot (native Protein with an exposed cysteine or obtained after modification of amino groups of the protein by SPDP for instance)----->saccharide-S—S-Prot
Saccharide-COOH+EDAC+NH2----SH----->saccharide----SH+maleimide-Prot (modification of amino groups)----> conjugate
Saccharide-Aldehyde+NH2-----NH2---->saccharide---NH2+EDAC+COOH-Prot---->conjugate As can be observed carbodiimide chemistry (e.g. using EDAC) is very convenient for conjugation reactions as it makes use of groups on the saccharide and/or protein which may be naturally present or easily inserted by derivatisation. It also conveniently links moieties through a peptide bond.

Carbodiimides (RN=C=NR') are unsaturated compounds with an allene structure (Nakajima and Ikada 1995 Bioconjugate Chem. 6:123-130; Hoare and Koshland 1967 JBC 242:2447-2453). The chemical is relatively unstable at its reaction pH (4.5-6.5), and therefore all components of the saccharide/protein/carbodiimide conjugation reaction tend to be added together in the art.

The present inventors have found that depending on the nature of the saccharide and protein to be conjugated, better characteristics of the final conjugate for vaccine use may be achieved by adding a certain component of the reaction slowly to the mix. In so doing one or more benefits/improvements may be realised such as: saccharide yield in the conjugate, sterile filterability of the conjugate, better control of the conjugation, easier reproducibility, and/or prevention of intra-moiety cross-links.

Accordingly, in one embodiment there is provided a method of conjugating a saccharide to a protein carrier using carbodiimide condensation chemistry, wherein the saccharide comprises (for instance as part of its repeating unit), or has been derivatised to comprise, amino and/or carboxyl groups, and wherein the protein carrier comprises, or has been derivatised to comprise, amino and/or carboxyl groups, comprising the steps of:
 I)—if the protein carrier comprises both amino and carboxyl groups and the saccharide comprises either amino or carboxyl groups:
  a) mixing the saccharide and aliquot of carbodiimide required to perform the conjugation, and
  b) adding the aliquot of protein carrier required over a period of 35 seconds to 6 hours;

II)—if the saccharide comprises both amino and carboxyl groups and the protein carrier comprises either amino or carboxyl groups:
a) mixing the protein carrier and aliquot of carbodiimide required to perform the conjugation, and
b) adding the aliquot of saccharide required over a period of 35 seconds to 6 hours;

III)—if the saccharide comprises both amino and carboxyl groups and the protein carrier comprises both amino and carboxyl groups:
a) mixing the protein carrier and saccharide, and
b) adding the aliquot of carbodiimide required to perform the conjugation over a period of 35 seconds to 6 hours.

DETAILED DESCRIPTION

Any suitable carbodiimide may be used as long as it is capable of conjugating saccharides and proteins in an aqueous medium. In one embodiment the carbodiimide may be EDAC (1-ethyl-3-(3-dimethyl-aminopropyl) carbodiimide) [also known as EDC] or it may be a carbodiimide other than EDAC.

The term "saccharide" throughout this specification may indicate polysaccharide or oligosaccharide and includes both. It may indicate lipopolysaccharide (LPS) or lipooliogosaccharide (LOS). Before use Polysaccharides (such as bacterial polysaccharides) may be isolated from a source strain (e.g. of bacteria) or isolated from the source strain and sized to some degree by known methods (see for example EP497524 and EP497525; Shousun Chen Szu et al.—Carbohydrate Research Vol 152 p 7-20 (1986)) for instance by microfluidisation. Polysaccharides can be sized in order to reduce viscosity in polysaccharide samples and/or to improve filterability for conjugated products. Oligosaccharides have a low number of repeat units (typically 5-30 repeat units) and are typically hydrolysed polysaccharides.

The term "protein carrier" is intended to cover both small peptides and large polypeptides (>10 kDa). Clearly large polypeptides are more likely to contain both reactive amino and carboxyl groups without any modification.

For the purposes of the invention, "native polysaccharide" refers to a saccharide that has not been subjected to a process, the purpose of which is to reduce the size of the saccharide. A polysaccharide can become slightly reduced in size during normal purification procedures. Such a saccharide is still native. Only if the polysaccharide has been subjected to sizing techniques would the polysaccharide not be considered native.

For the purposes of the invention, "sized by a factor up to ×2" means that the saccharide is subject to a process intended to reduce the size of the saccharide but to retain a size more than half the size of the native polysaccharide. ×3, ×4 etc. are to be interpreted in the same way i.e. the saccharide is subject to a process intended to reduce the size of the polysaccharide but to retain a size more than a third, a quarter etc. the size of the native polysaccharide.

The 35 second to 6 hour time period in step b) of the method for the addition of the full aliquot of the final component can be 50 seconds to 5 hours, 1 minute to 4 hours, 2 minutes to 3 hours, 3 minutes to 2 hours, 4 to 60 minutes, 5 to 50 minutes, 6 to 40 minutes, 7 to 30 minutes or 8 to 20 minutes. It may be 1 minute to 5 hours, 10 minutes to 4 hours, 20 minutes to 3 hours, 30 minutes to 2 hours, 40 to 90 minutes, or 50 to 70 minutes. This time can be adjusted according to the precise saccharide and protein being conjugated.

In one embodiment the aliquot of the final component (e.g. of carbodiimide, saccharide or protein) is added to the reaction mixture at a constant rate during the time period (this is conveniently achieved using a pump operating at a constant rate). Alternatively it may be added in stages over the time period. Although this may be done in many ways, in general parts of the aliquot should be added throughout the period. For instance at least one quarter of the aliquot may be added over the first half of the period, and at least one quarter of the aliquot over the second half of the period. The total amount of the aliquot 'a' measured, for instance, in mL or mg may be added in 4-100 stages ('s') throughout the period. In one embodiment the stages are arranged such that an even amount (a/s) is introduced at all the stages. In one embodiment the stages are evenly spaced throughout the period 'p' (in seconds). Thus if one stage takes place at time zero of the period 'p', then each subsequent stage could take place at a time which is $p/(s-1)$. The volume of the aliquot of the final component added in step b) may be adjusted in terms of ease of addition of the aliquot to the reaction within the desired time period. The carbodiimide may be added as an aqueous solution (typically buffered at pH 7.5 before being added to the reaction) or as solid powder (EDAC for instance is highly soluble in aqueous media). Of course if the carbodiimide is the last component added to the reaction (situation III step b)), a slow dissolving carbodiimide may be used such that the entire aliquot of powder is added to the reaction all at once but it dissolves at a rate consistent with the desired period over which the aliquot is to be made available to the reaction.

If the protein and/or saccharide has no amino or carboxyl groups (or only has one of these), it may be derivatised to give it one (or to give it the other it does not already have). For instance for a saccharide only comprising reactive hydroxyl groups (e.g. meningococcal serogroup A capsular saccharide), such a group should be used for derivatising on amino or carboxyl groups so that EDAC condensation may be carried out.

This may take place within a repeat subunit, or may be a group only present at the end of the saccharide molecule.

It should be noted that where derivatisation takes place, it can be beneficial to only partially derivatise the moiety. For saccharides with repeating subunits, the target epitope may be present in each repeat. Therefore if partial derivatisation takes place (for this it is meant 0.5-20, 1-15, 3-12, or 5-10% of the targeted reactive group is actually derivatised) this can have the benefit of conserving the majority of the epitopes, and preventing too much cross-linking.

If a saccharide or protein already has amino or carboxyl groups only (e.g. Vi saccharide from *Salmonella typhi* which naturally has carboxyl but not amino groups), derivatisation can take place to give it the other type of group (i.e. amino groups for Vi). It should be noted, however, that as derivatisation can be partial this action can change the preferred reaction of the invention from a type I to a type III. For instance if Vi saccharide is conjugated to a protein carrier comprising both amino and carboxyl groups situation I adds the aliquot of protein slowly in step b). If the Vi saccharide carboxyl group is partially derivatised with amino groups it will have both carboxyl and amino groups, thus situation III adding the aliquot of carbodiimide slowly in step b) becomes most relevant.

Derivatisation may occur through the addition of a hetero- or homo-bifunctional linker. It may take place with similar chemistry as described above for saccharide-protein conjugation step (e.g. CDAP or carbodiimide chemistry). The linker may have between 4 and 20, 4 and 12, or 5 and 10 carbon atoms. It may have two reactive amino groups, two reactive carboxyl groups, or one of each (e.g. hexane diamine, 6-aminocaproic acid, or adipic acid dihydrazide). Typically derivatization takes place through reacting a large excess of the linker with the saccharide and/or protein carrier to be derivatised. This allows derivatization to take place with minimal intra-moiety cross-linking (which otherwise might be possible if for instance a carboxyl group on a saccharide was being derivatised with amino groups using carbodiimide condensation). Excess linker is readily removed using techniques such as diafiltration.

In one embodiment the saccharide comprises a reactive hydroxyl group as part of its repeating unit which is partially derivatised via an amino group on the linker (e.g. with CDAP chemistry). In another embodiment the saccharide comprises a reactive amino group as part of its repeating unit which is partially derivatised via a carboxyl group on the linker (e.g. with carbodiimide chemistry). In a further embodiment the saccharide comprises a reactive carboxyl group as part of its repeating unit which is partially derivatised via an amino group on the linker (e.g. with carbodiimide chemistry).

The aliquot of carbodiimide required to perform the conjugation (whether present in step a) or b) of the reaction of the invention) is 0.01 to 3, 0.05 to 2, or 0.09 to 1 mg carbodiimide/mg saccharide. Although these numbers are calculated in respect of EDAC being the carbodiimide, these numbers may be adjusted if any other carbodiimide is used by multiplying the numbers in the range by: (molecular weight of other carbodiimide)/(molecular weight of EDAC).

In general, the saccharide may be present in the methods of the invention at a final concentration of 0.5-50 mg/ml in step b). This will depend on the size and nature of the saccharide, and the extent of any derivatisation. For instance for oligosaccharides a larger concentration will be required, but for large polysaccharides a much smaller concentration will be more appropriate. If it is towards the high end of partially derivatised with amino or carboxyl groups a smaller concentration may be appropriate to reduce the possibility of any cross-linking. The protein carrier may be present at a final concentration of 1-50 mg/ml in step b).

The initial ratio of protein carrier to saccharide in the methods of the invention can be 5:1 to 1:5, 4:1 to 1:1, or 3:1 to 2:1 (w/w). Again this will depend on the size and nature of the saccharide, and the extent of any derivatisation.

Salt conditions (e.g. NaCl) may also be varied according to the nature of the saccharide/protein. Usually around 0.2M NaCl may be present in step b) of the methods of the invention, but may be 0-2, 0.1-1 or 0.2-0.5 M.

In terms of pH in step b) of the methods of the invention, the reaction pH may be any pH where the carbodiimide is activated—for instance pH 4.5-6.5, 4.7-6.0, or 5-5.5. This pH is typically maintained throughout the reaction by addition of acid/base as required. EDAC is usually stable at pH 7.5, though if the conjugation requires to be done at higher pH compounds which are known to keep the reaction intermediate stable (such as N-hydroxysuccinimide) may also be present in the reaction in step b), in which case the reaction pH in step b) may be maintained at pH 4.5-7.5.

The reaction temperature during step b) of the methods of the invention can be 4-37, 10-32, 17-30, or 22-27° C., and is typically maintained throughout the reaction.

In the methods of the invention, once the entire aliquot has been added in step b) the reaction is typically maintained for a further 10 minutes to 72 hours, 20 minutes to 48 hours, 30 minutes to 24 hours, 40 minutes to 12 hours, 50 minutes to 6 hours, or 1-3 hours. Once the reaction is completed the pH is adjusted to 7.5-9 (towards the higher end of this if N-hydroxysuccinimide is present) to go back to the stable pH range of carbodiimide.

Once conjugated, the saccharide-protein conjugate may be purified from: unreacted components, free saccharide, etc by injecting it on a size exclusion chromatography column (for instance SEPHACRYL S400HR, Pharmacia). This is typically carried out at 2-8° C. The conjugate may be sterile filtered then stored. Ultimately an effective dose (for instance 1-20, 2-15, or 3-10 μg saccharide/dose) of the saccharide-protein conjugate can be formulated with a pharmaceutically acceptable excipient (for instance a salt or adjuvant) to manufacture an immunogenic composition or vaccine.

In terms of the saccharides of the invention, any saccharide of viral, fungal, bacterial or eukaryotic source may be conjugated using the methods of the invention. It may be the Vi saccharide from *Salmonella typhi*, or a saccharide other than Vi. It may be the capsular saccharide Hib from *H. influenzae* type b, or may be a saccharide other than Hib. In one embodiment the saccharide is a bacterial capsular saccharide, for instance derived from a bacterium selected from a list consisting of: *N. meningitidis* serogroup A (MenA), B (MenB), C (MenC), W135 (MenW) or Y (MenY), *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F or 33F, Group B *Streptococcus* group Ia, Ib, II, III, IV, V, VI, or VII, *Staphylococcus aureus* type 5, *Staphylococcus aureus* type 8, *Salmonella typhi* (Vi saccharide), *Vibrio cholerae*, or *H. influenzae* type b.

The weight-average molecular weight of the saccharide may be 1000-2000000, 5000-1000000, 10000-500000, 50000-400000, 75000-300000, or 100000-200000. The molecular weight or average molecular weight of a saccharide herein refers to the weight-average molecular weight (Mw) of the saccharide measured prior to conjugation and is measured by MALLS. The MALLS technique is well known in the art and is typically carried out as described in example 2. For MALLS analysis of saccharides, two columns (TSKG6000 and 5000PWxl) may be used in combination and the saccharides are eluted in water. Saccharides are detected using a light scattering detector (for instance Wyatt Dawn DSP equipped with a 10 mW argon laser at 488 nm) and an inferometric refractometer (for instance Wyatt Otilab DSP equipped with a P100 cell and a red filter at 498 nm). In an embodiment, the polydispersity of the saccharide is 1-1.5, 1-1.3, 1-1.2, 1-1.1 or 1-1.05 and after conjugation to a carrier protein, the polydispersity of the conjugate is 1.0-2.5, 1.0-2.0. 1.0-1.5, 1.0-1.2, 1.5-2.5, 1.7-2.2 or 1.5-2.0. All polydispersity measurements are by MALLS.

The saccharide may be either a native polysaccharide or may have been sized by a factor of no more than 2, 4, 6, 8, 10 or 20 fold (for instance by microfluidization [e.g. by EMULSIFLEX C-50 apparatus] or other known technique [for instance heat, chemical, oxidation, sonication methods]). Oligosaccharides may have been sized substantially further [for instance by known heat, chemical, or oxidation methods].

The structures of most of these saccharides are known (and therefore whether they naturally have any amino or carboxyl groups for carbodiimide chemistry, or any other reactive group which may be derivatised with amino or carboxyl groups (see table below).

| | Natural NH2 group | Natural COOH group | Other reactive group |
|---|---|---|---|
| S. aureus | | | |
| PS5 | No | Yes | OH |
| PS8 | No | Yes | OH |
| N. meningitidis | | | |
| MenA | No | No | OH |
| MenC | No | Yes | OH |
| MenW135 | No | Yes | OH |
| MenY | No | Yes | OH |
| MenB | No (can be generated if de-N-acetylated) | Yes | OH/N-propyl |

-continued

| | Natural NH2 group | Natural COOH group | Other reactive group |
|---|---|---|---|
| Gp. B Streptococcus | | | |
| Ia, Ib | No | Yes | OH |
| II | No | Yes | OH |
| III | No | Yes | OH |
| IV | No | Yes | OH |
| V | No | Yes | OH |
| VI | No | Yes | OH |
| VII | No | Yes | OH |
| S. typhi | | | |
| Vi | No | Yes | No |
| S. pneumoniae | | | |
| PS1 | Yes | Yes | OH |
| PS3, 4, 5, 8, 9, 12F | No | Yes | OH |
| Vibrio cholorea | | | |
| Capsular saccharide | yes | No | OH |
| H. influenzae B Hib LOS | No | No | OH |
| Nmen/Mcat/Hi | Yes on PEA | Yes on KDO | OH |

The saccharide may be a bacterial lipooligosaccharide or lipopolysaccharide (see above table), for instance derived from a bacterium selected from a list consisting of: N. meningitidis, H. influenzae, E. coli, Salmonella or M. catarrhalis. The LOS may be meningococcal immunotype L2, L3 or L10. It may be detoxified by alkaline treatment of its Lipid A moiety.

In an embodiment, the MenA capsular saccharide, is at least partially O-acetylated such that at least 50%, 60%, 70%, 80%, 90%, 95% or 98% of the repeat units are O-acetylated at least one position. O-acetylation is for example present at least at the 0-3 position of at least 50%, 60%, 70%, 80%, 90%, 95% or 98% of the repeat units. In an embodiment, the MenC capsular saccharide, is at least partially O-acetylated such that at least 30%, 40%, 50%, 60%, 70%, 80%, 90%, 95% or 98% of (α2→9)-linked NeuNAc repeat units are O-acetylated at least one or two positions. O-acetylation is for example present at the O-7 and/or O-8 position of at least 30%. 40%, 50%, 60%, 70%, 80%, 90%, 95% or 98% of the repeat units. In an embodiment, the MenW capsular saccharide, is at least partially O-acetylated such that at least 30%, 40%, 50%, 60%, 70%, 80%, 90%, 95% or 98% of the repeat units are O-acetylated at least one or two positions. O-acetylation is for example present at the O-7 and/or O-9 position of at least 30%. 40%, 50%, 60%, 70%, 80%, 90%, 95% or 98% of the repeat units. In an embodiment, the MenY capsular saccharide, is at least partially O-acetylated such that at least 20%, 30%, 40%, 50%, 60%, 70%, 80%, 90%, 95% or 98% of the repeat units are O-acetylated at least one or two positions. O-acetylation is present at the 7 and/or 9 position of at least 20%, 30%, 40%, 50%, 60%, 70%, 80%, 90%, 95% or 98% of the repeat units. The percentage of O-acetylation refers to the percentage of the repeat units containing O-acetylation. This may be measured in the saccharide prior to conjugate and/or after conjugation.

The protein carrier may be any peptide or protein. It may comprise one or more T-helper epitopes. In one embodiment of the invention the protein carrier is selected from the group consisting of: TT, DT, CRM197, fragment C of TT, protein D of H. influenzae, pneumococcal PhtD, and pneumococcal Pneumolysin. The carrier protein may be tetanus toxoid (TT), tetanus toxoid fragment C, non-toxic mutants of tetanus toxin [note all such variants of TT are considered to be the same type of carrier protein for the purposes of this invention], diphtheria toxoid (DT), CRM197, other non-toxic mutants of diphtheria toxin [such as CRM176, CRM 197, CRM228, CRM 45 (Uchida et al J. Biol. Chem. 218; 3838-3844, 1973); CRM 9, CRM 45, CRM102, CRM 103 and CRM107 and other mutations described by Nicholls and Youle in Genetically Engineered Toxins, Ed: Frankel, Maecel Dekker Inc, 1992; deletion or mutation of Glu-148 to Asp, Gln or Ser and/or Ala 158 to Gly and other mutations disclosed in U.S. Pat. No. 4,709,017 or U.S. Pat. No. 4,950,740; mutation of at least one or more residues Lys 516, Lys 526, Phe 530 and/or Lys 534 and other mutations disclosed in U.S. Pat. No. 5,917, 017 or U.S. Pat. No. 6,455,673; or fragment disclosed in U.S. Pat. No. 5,843,711] (note all such variants of DT are considered to be the same type of carrier protein for the purposes of this invention), pneumococcal pneumolysin (Kuo et al (1995) Infect Immun 63; 2706-13), OMPC (meningococcal outer membrane protein—usually extracted from N. meningitidis serogroup B—EP0372501), synthetic peptides (EP0378881, EP0427347), heat shock proteins (WO 93/17712, WO 94/03208), pertussis proteins (WO 98/58668, EP0471177), cytokines, lymphokines, growth factors or hormones (WO 91/01146), artificial proteins comprising multiple human CD4+ T cell epitopes from various pathogen derived antigens (Falugi et al (2001) Eur J Immunol 31; 3816-3824) such as N19 protein (Baraldoi et al (2004) Infect Immun 72; 4884-7) pneumococcal surface protein PspA (WO 02/091998), iron uptake proteins (WO 01/72337), toxin A or B of C. difficile (WO 00/61761), H. influenzae Protein D (EP594610 and WO 00/56360), pneumococcal PhtA (WO 98/18930, also referred to as Sp36), pneumococcal PhtD (disclosed in WO 00/37105, and is also referred to Sp036D), pneumococcal PhtB (disclosed in WO 00/37105, and is also referred to Sp036B), or PhtE (disclosed in WO00/30299 and is referred to as BVH-3).

In a further aspect of the invention there is provided a saccharide-protein carrier conjugate (or an immunogenic composition or vaccine) obtainable or obtained by the method of the invention.

A use of the immunogenic composition or vaccine of the invention in the manufacture of a medicament for the prevention or treatment of disease, and a method of preventing or treating disease comprising the step of administering an effective dose of the immunogenic composition or vaccine of the invention to a patient in need thereof is further provided. The use or method may be such that the disease is caused by a bacterium selected from a list consisting of: N. meningitidis, Streptococcus pneumoniae, M. catarrhalis, Group B Streptococcus, Staphylococcus aureus, Salmonella typhi, Vibrio cholerae, E. coli, and H. influenzae.

The immunogenic compositions of the invention may also comprise a DTPa or DTPw vaccine (for instance one containing DT, TT, and either a whole cell pertussis (Pw) vaccine or an acellular pertussis (Pa) vaccine (comprising for instance pertussis toxoid, FHA, pertactin, and, optionally agglutinogins 2 and 3). Such combinations may also comprise a vaccine against hepatitis B (for instance it may comprise hepatitis B surface antigen [HepB], optionally adsorbed onto aluminium phosphate). In one embodiment the immunogenic composition of the invention comprises Hib, MenA and MenC saccharide conjugates, or Hib and MenC saccharide conjugates, or Hib, MenC and MenY saccharide conjugates, or MenA, MenC, MenW and MenY saccharide conjugates, wherein at least one, two or all the saccharide conjugates are made according the method of the invention.

Immunogenic compositions of the invention optionally comprise additional viral antigens conferring protection against disease caused by measles and/or mumps and/or rubella and/or varicella. For example, immunogenic composition of the invention contains antigens from measles, mumps and rubella (MMR) or measles, mumps, rubella and varicella (MMRV). In an embodiment, these viral antigens are optionally present in the same container as the meningococcal and/or Hib saccharide conjugate(s) present in the composition. In an embodiment, these viral antigens are lyophilised.

In an embodiment, the immunogenic composition of the invention further comprises an antigen from *N. meningitidis* serogroup B. The antigen is optionally an outer membrane vesicle preparation from *N. meningitidis* serogroup B as described in EP301992, WO 01/09350, WO 04/14417, WO 04/14418 and WO 04/14419.

In general, the immunogenic composition of the invention may comprise a dose of each saccharide conjugate between 0.1 and 20 µg, 2 and 10 µg, 2 and 6 µg or 4 and 7 µg of saccharide.

"Around" or "approximately" are defined as within 10% more or less of the given figure for the purposes of the invention.

In an embodiment, the immunogenic composition of the invention is adjusted to or buffered at, or adjusted to between pH 7.0 and 8.0, pH 7.2 and 7.6 or around or exactly pH 7.4.

The immunogenic composition or vaccines of the invention are optionally lyophilised in the presence of a stabilising agent for example a polyol such as sucrose or trehalose.

Optionally, the immunogenic composition or vaccine of the invention contains an amount of an adjuvant sufficient to enhance the immune response to the immunogen. Suitable adjuvants include, but are not limited to, aluminium salts (aluminium phosphate or aluminium hydroxide), squalene mixtures (SAF-1), muramyl peptide, saponin derivatives, mycobacterium cell wall preparations, monophosphoryl lipid A, mycolic acid derivatives, non-ionic block copolymer surfactants, Quil A, cholera toxin B subunit, polyphosphazene and derivatives, and immunostimulating complexes (IS-COMs) such as those described by Takahashi et al. (1990) Nature 344:873-875.

For *N. meningitidis* or HibMen combinations, it may be advantageous not to use any aluminium salt adjuvant or any adjuvant at all.

As with all immunogenic compositions or vaccines, the immunologically effective amounts of the immunogens must be determined empirically. Factors to be considered include the immunogenicity, whether or not the immunogen will be complexed with or covalently attached to an adjuvant or carrier protein or other carrier, route of administrations and the number of immunising dosages to be administered.

The active agent can be present in varying concentrations in the pharmaceutical composition or vaccine of the invention. Typically, the minimum concentration of the substance is an amount necessary to achieve its intended use, while the maximum concentration is the maximum amount that will remain in solution or homogeneously suspended within the initial mixture. For instance, the minimum amount of a therapeutic agent is optionally one which will provide a single therapeutically effective dosage. For bioactive substances, the minimum concentration is an amount necessary for bioactivity upon reconstitution and the maximum concentration is at the point at which a homogeneous suspension cannot be maintained. In the case of single-dosed units, the amount is that of a single therapeutic application. Generally, it is expected that each dose will comprise 1-100 µg of protein antigen, optionally 5-50 µg or 5-25 µg. For example, doses of bacterial saccharides are 10-20 µg, 5-10 µg, 2.5-5 µg or 1-2.5 µg of saccharide in the conjugate.

The vaccine preparations of the present invention may be used to protect or treat a mammal (for example a human patient) susceptible to infection, by means of administering said vaccine via systemic or mucosal route. A human patient is optionally an infant (under 12 months), a toddler (12-24, 12-16 or 12-14 months), a child (2-10, 3-8 or 3-5 years) an adolescent (12-21, 14-20 or 15-19 years) or an adult. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance if saccharides are present in a vaccine these could be administered separately at the same time or 1-2 weeks after the administration of a bacterial protein vaccine for optimal coordination of the immune responses with respect to each other). In addition to a single route of administration, 2 different routes of administration may be used. For example, viral antigens may be administered ID (intradermal), whilst bacterial proteins may be administered IM (intramuscular) or IN (intranasal). If saccharides are present, they may be administered IM (or ID) and bacterial proteins may be administered IN (or ID). In addition, the vaccines of the invention may be administered IM for priming doses and IN for booster doses.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

A further aspect of the invention is a process for making the immunogenic composition or vaccine of the invention, comprising the step of mixing the MenA and MenC saccharides of the invention made by the method of the invention, with MenW and MenY that have not been made according to the invention, and with a pharmaceutically acceptable excipient.

The terms "comprising", "comprise" and "comprises" herein are intended by the inventors to be optionally substitutable with the terms "consisting of", "consist of" and "consists of", respectively, in every instance.

All references or patent applications cited within this patent specification are incorporated by reference herein.

The invention is illustrated in the accompanying examples. The examples below are carried out using standard techniques, which are well known and routine to those of skill in the art, except where otherwise described in detail. The examples are illustrative, but do not limit the invention.

EXAMPLES

Example 1

Preparation of Polysaccharide Conjugates

Example 1a

Preparation of Meningococcal MenA and MenC Capsular Polysaccharide Conjugate According to the Invention MenC-TT conjugates were produced using native polysaccharides (of over 150 kDa as measured by MALLS) or were slightly microfluidised. MenA-TT conjugates were produced using either native polysaccharide or slightly microfluidised polysaccharide of over 60 kDa as measured by the MALLS method of example 2. Sizing was by microfluidisation using a homogenizer Emulsiflex C-50 apparatus. The polysaccharides were then filtered through a 0.2 μm filter.

In order to conjugate MenA capsular polysaccharide to tetanus toxoid via a spacer, the following method was used. The covalent binding of the polysaccharide and the spacer (ADH) is carried out by a coupling chemistry by which the polysaccharide is activated under controlled conditions by a cyanylating agent, 1-cyano-4-dimethylamino-pyridinium tetrafluoroborate (CDAP). The spacer reacts with the cyanylated PS through its hydrazino groups, to form a stable isourea link between the spacer and the polysaccharide.

A 10 mg/ml solution of MenA (pH 6.0) [3.5 g] was treated with a freshly prepared 100 mg/ml solution of CDAP in acetonitrile/water (50/50 (v/v)) to obtain a CDAP/MenA ratio of 0.75 (w/w). After 1.5 minutes, the pH was raised to pH 10.0. Three minutes later, ADH was added to obtain an ADH/MenA ratio of 8.9. The pH of the solution was decreased to 8.75 and the reaction proceeded for 2 hours maintaining this pH (with temperature kept at 25° C.).

The $PSA_{AH}$ solution was concentrated to a quarter of its initial volume and then diafiltered with 30 volumes of 0.2M NaCl using a Filtron Omega membrane with a cut-off of 10 kDa, and the retentate was filtered.

Prior to the conjugation (carbodiimide condensation) reaction, the purified TT solution and the $PSA_{AH}$ solution were diluted to reach a concentration of 10 mg/ml for $PSA_{AH}$ and 10 mg/ml for TT.

EDAC (1-ethyl-3-(3-dimethyl-aminopropyl) carbodiimide) was added to the $PS_{AH}$ solution (2 g saccharide) in order to reach a final ratio of 0.9 mg EDAC/mg $PSA_{AH}$. The pH was adjusted to 5.0. The purified tetanus toxoid was added with a peristaltic pump (in 60 minutes) to reach 2 mg TT/mg $PSA_{AH}$. The resulting solution was left 60 min at +25° C. under stirring to obtain a final coupling time of 120 min. The solution was neutralised by addition of 1M Tris-Hcl pH 7.5 (1/10 of the final volume) and left 30 minutes at +25° C. then overnight at +2° C. to +8° C.

The conjugate was clarified using a 10 μm filter and was purified using a SEPHACRYL S400HR column (Pharmacia, Sweden). The column was equilibrated in 10 mM Tris-HCl (pH 7.0), 0.075 M NaCl and the conjugate (approx. 660 mL) was loaded on the column (+2° C. to +8° C.). The elution pool was selected as a function of optical density at 280 nm. Collection started when absorbance increased to 0.05. Harvest continued until the Kd reached 0.30. The conjugate was filter sterilised at +20° C., then stored at +2° C. to +8° C. The resultant conjugate had a polysaccharide:protein ratio of 1:2-1:4 (w/w).

In order to conjugate MenC capsular polysaccharide to tetanus toxoid via a spacer, the following method was used. The covalent binding of the polysaccharide and the spacer (ADH) is carried out by a coupling chemistry by which the polysaccharide is activated under controlled conditions by a cyanylating agent, 1-cyano-4-dimethylamino-pyridinium tetrafluoroborate (CDAP). The spacer reacts with the cyanylated PS through its hydrazino groups, to form a stable isourea link between the spacer and the polysaccharide.

A 20 mg/ml solution of MenC (pH6.0) (3.5 g) was treated with a freshly prepared 100 mg/ml solution of CDAP in acetonitrile/water (50/50 (v/v)) to obtain a CDAP/MenC ratio of 1.5 (w/w). After 1.5 minutes, the pH was raised to pH 10.0. At activation pH 5M NaCl was added to achieve a final concentration of 2M NaCl. Three minutes later, ADH was added to obtain an ADH/MenC ratio of 8.9. The pH of the solution was decreased to 8.75 and the reaction proceeded for 2 hours (retained at 25° C.).

The $PSC_{AH}$ solution was concentrated to a minimum of 150 mL and then diafiltered with 30 volumes of 0.2M NaCl using a Filtron Omega membrane with a cut-off of 10 kDa, and the retentate was filtered.

Prior to the conjugation reaction, the purified TT solution and the $PSC_{AH}$ solution (2 g scale) were diluted in 0.2M NaCl to reach a concentration of 15 mg/ml for $PSC_{AH}$ and 20 mg/ml for TT.

The purified tetanus toxoid was added to the $PSC_{AH}$ solution in order to reach 2 mg TT/mg $PSC_{AH}$. The pH was adjusted to 5.0. EDAC (16.7 mg/ml in Tris 0.1M pH 7.5) was added with a peristaltic pump (in 10 minutes) to reach a final ratio of 0.5 mg EDAC/mg $PSC_{AH}$. The resulting solution was left 110 min at +25° C. under stirring and pH regulation to obtain a final coupling time of 120 min. The solution was then neutralized by addition of 1M Tris-Hcl pH 9.0 (1/10 of final volume) and left 30 minutes at +25° C. then overnight at +2° C. to +8° C.

The conjugate was clarified using a 10.1m filter and was purified using a SEPHACRYL S400HR column (Pharmacia, Sweden). The column was equilibrated in 10 mM Tris-HCl (pH 7.0), 0.075 M NaCl and the conjugate (approx. 460 mL) was loaded on the column (+2° C. to +8° C.). The elution pool was selected as a function of optical density at 280 nm. Collection started when absorbance increased to 0.05. Harvest continued until the Kd reached 0.20. The conjugate was filter sterilised at +20° C., then stored at +2° C. to +8° C. The resultant conjugate had a polysaccharide:protein ratio of 1:2-1:4 (w/w).

Various experiments adding EDAC over 10-45 minutes were carried out—in each case good quality MenC conjugates resulted. If, however the TT carrier was added last slowly to the MenC-ADH+EDAC mix this led to a gel—a conjugate that could not be purified.

Experiments were also carried out adding the EDAC all at once into the reaction but the final TT/PS ratio (2.7/1) (w/w) of the conjugate was lower than for the conjugate obtained via the reaction where EDAC was added over 10 minutes (3.3/1); furthermore the aTT and aPS antigenicity were both lower than that measured in respect of the conjugate made by the reaction where EDAC was added over 10 minutes.

Note on Approximate % Derivatisation of the Polysaccharides

MenCAH: after CDAP treatment with ADH about 3.47% of hydroxyl groups were derivatized with ADH (with an estimation of two available hydroxyl groups per repeat subunit). For MenA: about 11.5% of hydroxyl groups derivatized with ADH (considering there is only one available hydroxyl group per repeat unit).

Example 1b

Preparation of Pneumococcal Capsular PS 3 Polysaccharide Conjugate

1) $PSO_3$-$TT_{AH}$ process: $PSO_3$-$TT_{AH}$208
Sizing by Emulsiflex

PS was weighed on the basis of 10% theoretical moisture content. The native PS was dissolved overnight in 2M NaCl at an initial concentration of 3 mg/ml. Before sizing, the solution of native PS was clarified on 5 μm cut-off filter.

A homogenizer EMULSIFLEX C-50 apparatus was used to reduce the molecular weight and the viscosity of the polysaccharide before the activation step. The efficiency of the sizing depends on the circuit pressure, the plunger alimentation pressure and on the total cycles number. In order to improve the efficiency of sizing (and consequently reduce the total number of cycles), the homogenizing cell of Emulsiflex was replaced with a cell with a fixed geometry (Microfluidics F20Y-0.75 μm interaction chamber). The aim of the sizing was to reduce the molecular weight and the viscosity of the PS without a critical decrease of its antigenicity.

The size reduction was done at 6000±500 psi and followed in process by a measure of viscosity. The sizing was stopped when the target of 2.0±0.2 cp was reached.

Filtration of Sized PS on 0.22 μm

Sized PS was filtered on a Millipak 40 membrane (cut-off 0.22 mm) at a flow-rate of 10 ml/min.

TT Derivatization

The derivatization step was performed at 25° C. under continuous stirring in a T° controlled waterbath. TT was diluted in NaCl 0.2M to obtain a final TT concentration of 25 mg/ml. ADH was added in solid form to the TT solution to reach a 0.2M final concentration. After complete ADH dissolution, the solution was set at pH 6.2+/−0.1 with HCl.

EDAC was then added to the TT/ADH solution to reach a final 0.02M concentration. The pH was set at 6.2+/−0.1 with HCl and was kept under pH regulation during 1 hour.

After the derivatization step, the pH was raised up to pH9.5 with NaOH to stop the reaction. The solution was left during 2 hours under pH regulation before the diafiltration step.

Diafiltration $TT_{AH}$ derivative was diafiltered in order to remove unreacted ADH and EDAC by-products. The diafiltration was performed on a centramate membrane (0.09 m$^2$, 10 kDa cut-off). The solution was dialysed against 20 volumes of 0.2M NaCl.

The follow-up of the diafiltration step was performed by a quantification of ADH (TNBS assay) in the permeate after 5, 10, 15 and 20 volumes of diafiltration.

Filtration on 0.22 μm $TT_{AH}$ was finally filtered on 0.22 μm cut-off membrane (Millipack 40) at a flow-rate of 10 ml/min. The filtered $TT_{AH}$ was then stored at −70° C.

PS3-$TT_{AH}$ Conjugate

The conditions of process were the following:

An initial PS3 concentration of 2 mg/ml in 0.2 M NaCl, an initial $TT_{AH}$/PS3 ratio of 1.5/1 (w/w), an EDAC concentration of 0.5 mg/mg PS, and a TT concentration of 10 mg/ml in 0.2M NaCl.

50 mg of PS3 were diluted in 2M NaCl to obtain a final PS concentration of 2 mg/ml. The purified $TT_{AH}$ solution was diluted in 0.2M NaCl to reach a concentration of 10 mg/ml.

The PS3 solution was adjusted to pH5 with HCl.

EDAC was added in solid form to the PS3 solution in order to reach a final concentration of 0.5 mg EDAC/mg PS. The pH was adjusted to 5.0±0.05 with HCl and $TT_{AH}$ was manually added in 11 minutes (aliquots/min). The resulting solution was incubated 109 min at +25° C. with stirring and pH regulation to obtain a final coupling time of 120 min. Then the solution was neutralized by addition of 1M Tris-HCl pH 7.5 and left 30 min at +25° C. The conjugate was finally clarified on a 5 μm membrane and injected on a Sephacryl S400HR column.

2) $PSO_3$-$TT_{AH}$ Process: $PS03_{AH}$-TT215

Sizing by Emulsiflex

As above.

Filtration of Sized PS on 0.22 μm

As above.

PS3 Derivatization

The derivatization step was performed at 25° C. under continuous stirring in a T° controlled waterbath. PS3 was diluted in NaCl 2M to obtain a final PS concentration of 3 mg/ml. The PS solution was set at pH6.0 before the addition of CDAP (0.25 mg/mg PS, dissolution at 100 mg/ml in a mix of acetonitrile/WFI). The pH was increased to pH9.5 with NaOH before the addition of ADH (8.9 mg ADH/mg PS, dissolution at 100 mg/ml in 0.2M NaCl). The pH was kept at 9.5 and regulated during 60 minutes. The percentage of derivatization corresponded to 2.4% (2.4 mg ADH/100 mg PS). This can be measured with known techniques: TNBS for the estimating ADH; and DMAB or resorcinol (Monsigny et al (1988) Anal. Biochem. 175, 525-530) for the PS quantification. In this case, TNBS dosage was 228 μg/ml and PS dosage: 5250 μg/ml.

Given the Mw of ADH is 174.2, and the Mw of the repeat unit of PS3 is 338.27 (having 1 COOH and 4 OH groups), there is 1.3 μmoles of ADH/15.52 μmole of repeat unit, or 1.3 μmoles of ADH/62.08 μmole of reactive hydroxyl group. 2.09% of PS3 hydroxyl groups were ADH modified hydroxyl groups.

Diafiltration $PS3_{AH}$ derivative was diafiltered in order to remove unreacted ADH and CDAP by-products. The diafiltration was performed on a UFP-30-C—H24LA membrane (42 cm$^2$, 30 kDa cut-off). The solution was dialysed against 20 volumes of 0.2M NaCl.

The follow-up of the diafiltration step was performed by a quantification of ADH (TNBS assay) in the permeate after 5, 10, 15 and 20 volumes of diafiltration.

Filtration on 0.22 μm $PS_{AH}$ was finally filtered on 0.22 μm cut-off membrane (Millipack 40) at a flow-rate of 10 ml/min. The filtered $PS3_{AH}$ was then stored at 4° C.

$PS3_{AH}$-TT Conjugate

The conditions of the process were the following:

An initial PS3 concentration of 2 mg/ml in 0.2 M NaCl, an initial TT/$PS3_{AH}$ ratio of 1.5/1 (w/w), an EDAC concentration of 0.5 mg/mg PS, and a TT concentration of 10 mg/ml in 0.2M NaCl.

50 mg of $PS3_{AH}$ was diluted in 0.2M NaCl to obtain a final PS concentration of 2 mg/ml. The purified TT solution was diluted in 0.2M NaCl to reach a concentration of 10 mg/ml.

The $PS3_{AH}$ solution was adjusted to pH5 with HCl.

EDAC was added in solid form to the $PS3_{AH}$ solution in order to reach a final concentration of 0.5 mg EDAC/mg PS. The pH was adjusted to 5.0±0.05 with HCl and TT was added in 10 minutes using a peristaltic pump. The resulting solution was incubated 110 min at +25° C. with stirring and pH regulation to obtain a final coupling time of 120 min. Then the solution was neutralized by addition of 1M Tris-HCl pH 7.5 and left 30 min at +25° C. The conjugate was finally clarified on a 5 μm membrane and injected on a Sephacryl S400HR column.

3 $PS03_{AH}$-TT Process: $PS3_{AH}$-TT217

Sizing by Emulsiflex

As above.

Filtration of Sized PS on 0.22 μm

As above.

PS3 Derivatization

As for 215 conjugate.

Diafiltration

As for 215 conjugate.

Filtration on 0.22 μm

As for 215 conjugate.

PS3$_{AH}$-TT Conjugate

The conditions of the process were the following:

An initial PS3 concentration of 2 mg/ml in 2 M NaCl, an initial TT/PS3$_{AH}$ ratio of 1.5/1 (w/w), an EDAC concentration of 0.5 mg/mg PS, and a TT concentration of 10 mg/ml in 0.15M NaCl.

50 mg of PS3$_{AH}$ was diluted in 0.2M NaCl to obtain a final PS concentration of 2 mg/ml. The purified TT solution was diluted in 0.2M NaCl to reach a concentration of 10 mg/ml.

The PS3$_{AH}$ and TT solutions were mixed and adjusted to pH5 with HCl.

EDAC was dissolved in a Tris 1M pH7.5 buffer. 40 μl of EDAC were added each minute (10 minutes to reach the EDAC/PS ratio (0.5 mg EDAC/mg PS)). The resulting solution was incubated 110 min at +25° C. under stirring and pH regulation to obtain a final coupling time of 120 min. Then the solution was neutralized by addition of 1M Tris-HCl pH 7.5 and left 30 min at +25° C. The conjugate was finally clarified on a 5 μm membrane and injected on a Sephacryl S400HR column.

4) PS03$_{AH}$-TT Process: PS3$_{AH}$-TT218

Sizing by Emulsiflex

As above.

Filtration of Sized PS on 0.22 μm

As above.

PS3 Derivatization

The derivatization step was performed at 25° C. with continuous stirring in a T° controlled waterbath. PS3 was diluted in NaCl 2M to obtain a final PS concentration of 3 mg/ml. EDAC was added in solid form to reach an EDAC/PS ratio of 0.1 mg/mg PS. After complete dissolution, the pH of the solution was set at 5. ADH (8.9 mg ADH/mg PS, dissolution at 100 mg/ml in 0.2M NaCl) was then added using a peristaltic pump in 44 minutes (though as such an excess of ADH was present, direct addition would also have been OK). The pH was kept at 5.0+/−0.1 and regulated during 120 minutes (44'+76'). The reaction was stopped by increasing the pH to 7.5 using sodium hydroxide. The percentage of derivatization corresponded to 3.7% (mg ADH/mg PS). TNBS dosage was 220 μg/ml and PS dosage was 5902 μg/ml, thus there is 1.26 μmoles of ADH/17.44 μmole of repeat unit (=μmole of reactive COOH group). Thus, 7.22% of PS3 carboxyl groups were ADH modified COOH groups.

Diafiltration

PS3$_{AH}$ derivative was diafiltered in order to remove unreacted ADH and EDAC by-products. The diafiltration was performed on a UFP-30-C—H24LA membrane (42 cm$^2$, 30 kDa cut-off). The solution was dialysed against 23 volumes of 0.2M NaCl.

The follow-up of the diafiltration step was performed by a quantification of ADH (TNBS assay) in the permeate after 5, 10, 15 and 20 volumes of diafiltration Filtration on 0.22 μm PS$_{AH}$ was finally filtered on 0.22 μm cut-off membrane (Millipack 40) at a flow-rate of 10 ml/min. The filtered PS3$_{AH}$ was then stored at 4° C.

PS3$_{AH}$-TT Conjugate

The conditions of the process were the following:

An initial PS3$_{AH}$ concentration of 2 mg/ml in 0.2 M NaCl, an initial TT/PS3$_{AH}$ ratio of 1.5/1 (w/w), an EDAC concentration of 0.5 mg/mg PS, and a TT concentration of 10 mg/ml in 0.2M NaCl.

50 mg of PS3$_{AH}$ was diluted in 0.2M NaCl to obtain a final PS concentration of 2 mg/ml. The purified TT solution was diluted in 0.2M NaCl to reach a concentration of 10 mg/ml.

The PS3$_{AH}$ and TT solutions were mixed together.

The pH was adjusted to 5.0±0.05 with HCl and EDAC was manually added in 10 minutes (equal part-aliquots added each minute). The resulting solution was incubated 110 min at +25° C. with stirring and pH regulation to obtain a final coupling time of 120 min. Then the solution was neutralized by addition of 1M Tris-HCl pH 7.5 and left 30 min at +25° C. The conjugate was finally clarified on a 5 μm membrane and injected on a Sephacryl S400HR column.

Conclusions:

Different conjugates were made using carbodiimide chemistry in the conjugation step. The last component added in the reaction solution can be either the TT protein or the EDAC reagent. The time of addition can have an effect on the resulting conjugates.

PS3$_{AH}$TT215 & 217 Conjugates:

The same components and conditions were used to prepare both conjugates. The way in which the last component was added was different. PS3$_{AH}$TT217 conjugate led to a product which met in-vitro criteria. This one was made by adding EDAC in 10 minutes. PS3$_{AH}$TT215 conjugate, however, could not be filtered on sterile membrane. For this one, the last component added in the reaction medium was the TT (in 10 minutes).

Final TT/PS ratios were highly different for both conjugates. (0.98/1 vs 0.50/1). If EDAC is added first to the PS$_{AH}$ (having both reactive amino and carboxyl groups) this can lead to intra cross-linking of hydrazine and carboxylic groups present on the polysaccharide, and thus could lead to a more cross-linked conjugate with a weaker final ratio after the addition of TT in 10 minutes.

This effect is not observed for the PS3$_{AH}$TT217 conjugate. The TT incorporation worked better by the addition of EDAC in 10 minutes, perhaps due to lower intra cross-linking, and better inter cross-linking between hydrazine groups of the PS3$_{AH}$ and carboxylic groups of the protein.

In the case of the 218 conjugate, as the PS3 EDAC derivatisation only partially derivatises the polysaccharide (to keep the majority of the polysaccharides epitopes intact), again both reactive amino and carboxyl groups are present, hence why slow addition of EDAC in a final conjugation step is also beneficial.

Slow TT addition in the final conjugation step was beneficial (however) for the 208 conjugate where the TT was ADH derivatised (and comprises amino and carboxyl groups), whereas the PS3 was left with its native reactive —OH and —COOH groups as part of its repeating subunit. The addition of EDAC to PS 3 did not have the above cross-linking effect, and the slow addition of the derivatised TT yielded conjugate with good in vitro characteristics—see below.

In-Vitro Characterization:

| Conj. | Derivatization/ Chemistry | Conjugation/ Chemistry | Final component addition |
|---|---|---|---|
| 208 | TT/ADH → EDAC | PS-TT$_{AH}$ → EDAC | TT$_{AH}$ added in 11 minutes |
| 215 | PS3/ADH → CDAP | PS$_{AH}$-TT → EDAC | TT added in 10 minutes |
| 217 | PS3/ADH → CDAP | PS$_{AH}$-TT → EDAC | EDAC added in 10 minutes |
| 218 | PS3/ADH → EDAC | PS$_{AH}$-TT → EDAC | EDAC added in 10 minutes |

| Conj. | PS | [PS] (mg/ml) | [TT] (mg/ml) | In.TT/PS ratio (w/w) | [EDAC] (mg/mg PS) | Coupl. time (min) |
|---|---|---|---|---|---|---|
| 208 | C6E02 | 2.0 | 10 (TT$_{AH}$), pump | 1.5/1 | 0.5/1 | 120 |
| 215 | 3$_{AH}$001 (CDAP) | 2.0 | 10 pump | 1.5/1 | 0.5/1 | 120 |
| 217 | 3$_{AH}$001 (CDAP) | 2.0 | 10 | 1.5/1 | 0.5/1 (Fractions) | 120 |
| 218 | 3$_{AH}$002 (EDAC) | 2.0 | 10 | 1.5/1 | 0.5/1 (Fractions) | 120 |

| Conj. | F.TT/PS ratio (w/w) | Yield PS rec (%) | Filtr. yield rec (%) | Free PS (%) | αPS/αPS (%) Antigenicity | αTT/αPS (%) Antigenicity |
|---|---|---|---|---|---|---|
| 208 | 1.84/1 | 69 | 95 | 10.2 | 99 | 103 100* |
| 215 | 0.50/1 | 17 | 27 | — | — | — |
| 217 | 0.98/1 | 66 | 100 | 0.7 | 17 | 103 100* |
| 218 | 0.88/1 | 74 | 101 | 11.0 | 34 | 222 216* |

*relative to the 208 conjugate

Example 1c

Preparation of *S. typhi* Vi Polysaccharide Conjugate of the Invention

Sizing by Emulsiflex

PS was weighed on the basis of 15% theoretical moisture content. The native PS is dissolved overnight in WFI at an initial concentration of 7 mg/ml. Before the sizing, the solution of native PS is clarified on 10 μm cut-off filter at a flow-rate of 50 ml/min. A homogenizer EMULSIFLEX C-50 apparatus was used to reduce the molecular weight and the viscosity of the polysaccharide before the activation step. The efficiency of the sizing depends on the circuit pressure, the plunger alimentation pressure and on the total cycles number. In order to improve the efficiency of sizing (and consequently reduce the total number of cycles), the homogenizing cell of Emulsiflex was replaced by a cell with a fixed geometry (Microfluidics F20Y-0.75 μm interaction chamber). The aim of the sizing is to reduce the molecular weight and the viscosity of the PS without a critical decrease of its antigenicity.

The size reduction was realized at 15000±500 psi and followed in process by a measure of viscosity. The sizing is stopped when the target of 5.0±0.3 cp is reached.

Filtration of sized PS on 0.22 μm

Sized PS is filtered on a Millipak 40 membrane (cut-off 0.22 mm) at a flow-rate of 10 ml/min. The filtered sized PS is stored at −20° C.

Derivatization of Polysaccharide Vi 1.5 g of sized Vi PS was dissolved at 25° C. in EPI under agitation (5 mg/ml). 13.35 g of ADH (8.9 mg ADH/mg PS) is added to the PS solution. After complete dissolution pH was adjusted at pH 5.0±0.05 with 1N HCl. EDAC (0.1 mg/mg PS) was added in a solid form. The solution was left 60 min at 25° C. Then the solution was neutralized by addition of 1M Tris-HCl pH 7.5 and left at least 30 min at 25° C. (maximum 2 hours). The level of derivatization was estimated to be 4.55% using the TNBS dosage (mg ADH/100 mg PS). TNBS dosage was 200 μg/ml and PS dosage was 4034 μg/ml; thus 0.0697 μmoles of ADH/16.46 μmole of repeat unit (Mw 245). 1.3 μmoles of ADH/16.46 μmole of reactive COOH group on Vi, thus 7% of Vi COOH groups were ADH modified COOH groups.

Diafiltration

PSVi$_{AH}$ derivative was diafiltered in order to remove unreacted ADH and EDAC by-products. The diafiltration was performed on a centramate membrane (0.09 m², 10 kDa cut-off). The solution was dialysed against 20 volumes of 0.2M NaCl.

The follow-up of the diafiltration step was performed by a quantification of ADH (TNBS assay) in the permeate after 3, 5, 10 and 20 volumes of diafiltration Filtration on 0.22 μm PSVi$_{AH}$ was finally filtered on 0.22 μm cut-off membrane (Millipack 40) at a flow-rate of 10 ml/min. The filtered PSViAH was stored at +2/+8° C. for a maximum of 4 days.

PSVi$_{AH}$-TT Conjugates

The conditions of process were the following:

An initial PSViAH concentration of 2 mg/ml in 0.2 M NaCl, an initial TT/PSViAH ratio of 2.5/1 (w/w), an EDAC concentration of 0.25 mg/mg PS and a TT concentration of 10 mg/ml in 0.2M NaCl.

1 g of PSVi$_{AH}$ was diluted in 0.2M NaCl to obtain a final PS concentration of 2 mg/ml (uronic acid dosage). The purified TT solution was diluted in 0.2M NaCl to reach a concentration of 10 mg/ml.

TT was added to the PSVi$_{AH}$ solution in order to reach a final ratio of 2.5 mg TT/mg PS. The pH is adjusted to 5.0±0.05 with 1N HCl. The EDAC solution (7.5 mg/ml in 0.1M Tris pH 7.5) was then added (in 10 minutes with a peristaltic pump) to reach 0.25 mg EDAC/mg PSVi$_{AH}$. The resulting solution was incubated 50 min at +25° C. with stirring and pH regulation to obtain a final coupling time of 60 min. Then the solution was neutralized by addition of 1M Tris-HCl pH 7.5 and left 30 min at +25° C. The conjugate was transferred at 4° C. and is left overnight under continuous slow stirring before the chromatography step.

Purification

Prior to the elution on Sephacryl S400HR, the conjugate was clarified using a 10 μm Kleenpak filter. The flow rate was fixed at 100 ml/min. The conjugate was then injected on Sephacryl S400HR and the collection pool was based on a Kd value. The following criterion was used for the pool collection: from OD=0.05 at 280 nm harvesting started, and finished when Kd=0.22.

Sterilizing Filtration

Before filtration, the bulk was brought back to room temperature. Then the conjugate was filtered on an Opticap 4" sterilizing membrane. The flow rate was fixed at 30 ml/min.

Analytical

The resulting conjugate had a final TT/PS ratio (w/w) of 2.44/1, a free PS content of 3.7% and a αPS/αPS antigenicity of 58%.

Example 1d

Preparation of Other Polysaccharide Conjugates

The covalent binding of *Haemophilus influenzae* (Hib) PRP polysaccharide to TT was carried out by a coupling chemistry developed by Chu et al (Infection and Immunity 1983, 40 (1); 245-256). Hib PRP polysaccharide was activated by adding CNBr and incubating at pH10.5 for 6 minutes. The pH was lowered to pH8.75 and adipic acid dihydrazide (ADH) was added and incubation continued for a further 90 minutes. The activated PRP was coupled to purifed tetanus toxoid via carbodiimide condensation using 1-ethyl-3-(3-dimethyl-aminopropyl)carbodiimide (EDAC). EDAC was added to the activated PRP to reach a final ratio of 0.6 mg EDAC/mg activated PRP. The pH was adjusted to 5.0 and purified tetanus toxoid was added to reach 2 mg TT/mg activated PRP. The resulting solution was left for three days with mild stirring. After filtration through a 0.45 μm membrane, the conjugate was purifed on a sephacryl S500HR (Pharmacia, Sweden) column equilibrated in 0.2M NaCl.

MenC-TT conjugates were produced using native polysaccharides (of over 150 kDa as measured by MALLS) or were slightly microfluidised. MenA-TT conjugates were produced using either native polysaccharide or slightly microfluidised polysaccharide of over 60 kDa as measured by the MALLS method of example 2. MenW and MenY-TT conjugates were produced using sized polysaccharides of around 100-200 kDa as measured by MALLS (see example 2). Sizing was by microfluidisation using a homogenizer Emulsiflex C-50 apparatus. The polysaccharides were then filtered through a 0.2 μm filter.

Activation and direct coupling were performed as described in WO96/29094 and WO 00/56360. Briefly, the polysaccharide at a concentration of 10-20 mg/ml in 2M NaCl pH 5.5-6.0 was mixed with CDAP solution (100 mg/ml freshly prepared in acetonitrile/WFI, 50/50) to a final CDAP/polysaccharide ratio of 0.75/1 or 1.5/1. After 1.5 minutes, the pH was raised with sodium hydroxide to pH10.0. After three minutes tetanus toxoid was added to reach a protein/polysaccharide ratio of 1.5/1 for MenW, 1.2/1 for MenY, 1.5/1 for MenA or 1.5/1 for MenC. The reaction continued for one to two hours.

After the coupling step, glycine was added to a final ratio of glycine/PS (w/w) of 7.5/1 and the pH was adjusted to pH9.0. The mixture was left for 30 minutes. The conjugate was clarified using a 10 μm Kleenpak filter and was then loaded onto a Sephacryl S400HR column using an elution buffer of 150 mM NaCl, 10 mM or 5 mM Tris pH7.5. Clinical lots were filtered on an Opticap 4 sterilizing membrane. The resultant conjugates had an average polysaccharide:protein ratio of 1:1-1:5 (w/w).

Example 2

Determination of Molecular Weight Using Malls

Detectors were coupled to a HPLC size exclusion column from which the samples were eluted. On one hand, the laser light scattering detector measured the light intensities scattered at 16 angles by the macromolecular solution and on the other hand, an interferometric refractometer placed on-line allowed the determination of the quantity of sample eluted. From these intensities, the size and shape of the macromolecules in solution can be determined.

The mean molecular weight in weight ($M_w$) is defined as the sum of the weights of all the species multiplied by their respective molecular weight and divided by the sum of weights of all the species.

a) Weight-average molecular weight: -Mw- $$M_w = \frac{\sum W_i \cdot M_i}{\sum W_i} = \frac{m_2}{m_1}$$

b) Number-average molecular weight: -Mn- $$M_n = \frac{\sum N_i \cdot M_i}{\sum N_i} = \frac{m_1}{m_0}$$

c) Root mean square radius: -Rw- and $R^2w$ is the square radius defined by:

$$R^2w \text{ or } (r^2)w = \frac{\sum m_i \cdot r_i^2}{\sum m_i}$$

(-$m_i$- is the mass of a scattering centre i and -$r_i$- is the distance between the scattering centre i and the center of gravity of the macromolecule).

d) The polydispersity is defined as the ratio -Mw/Mn-.

Meningococcal polysaccharides were analysed by MALLS by loading onto two HPLC columns (TSKG6000 and 5000PWxl) used in combination. 25 μl of the polysaccharide were loaded onto the column and was eluted with 0.75 ml of filtered water. The polysaccharides are detected using a light scattering detector (Wyatt Dawn DSP equipped with a 10 mW argon laser at 488 nm) and an inferometric refractometer (Wyatt Otilab DSP equipped with a P100 cell and a red filter at 498 nm).

The molecular weight polydispersities and recoveries of all samples were calculated by the Debye method using a polynomial fit order of 1 in the Astra 4.72 software.

Example 3

Clinical Trial Assessing the Effect of a Linker in MenA in a MenACWY Conjugate Vaccine A single dose of different formulations of MenACWY vaccine was administered to teenagers of 15-19 years in 5 groups of 25 subjects in a 1:1:1:1:1 randomised trial. The formulations tested were:

F1—MenACWY conjugated to tetanus toxoid with the MenA conjugate containing an AH (ADH) spacer (made according to example 1)—5/5/5/5 μg F2—MenACWY conjugated to tetanus toxoid with the MenA conjugate containing an AH spacer (made according to example 1)—2.5/5/2.5/2.5 μg F3—MenACWY conjugated to tetanus toxoid with the MenA conjugate containing an AH spacer (made according to example 1)—5/5/2.5/2.5 μg F4—MenACWY conjugated to tetanus toxoid with no spacer in any conjugate—5/5/5/5 μg Control group—Mencevax™ ACWY On day 30 after inoculation, a blood sample was taken from the patients.

The blood samples were used to assess the percentage of SBA-MenA, SBA-MenC, SBA-MenW135 and SBA-MenY responders one month after the vaccine dose. A vaccine response was defined as 1) for initially seronegative subjects—a post-vaccination antibody titre$\geq$1/32 at 1 month or 2) for initially seropositive subjects—antibody titre of $\geq$4 fold the pre-vaccination antibody titre.

Results

As shown in the Table below, the use of a spacer in the MenA conjugate led to an increased immune response against MenA. The percentage of responders rose from 66% to 90-95% when the AH spacer was added. This was reflected in an increase in SBA GMT from 4335 to 10000 and an increase in GMC from 5 to 20-40. Surprisingly, the use of a AH spacer also led to an increased immune response against MenC as seen by an increase in the percentage of responders and an increase in the SBA GMT. An increase could also be seen in the SBA-GMT against MenY (6742-7122) and against MenW (4621-5418) when a spacer was introduced.

| Formulation | % SBA MenA responders | SBA-MenA MenA GMT | Anti-PSA CMC µg/ml ELISA |
|---|---|---|---|
| F 1 5AH/5/5/5 | 90.9 | 9805 | 20.38 |
| F2 2.5AH/5/2.5/2.5 | 75 | 8517 | 29.5 |
| F3 5AH/5/2.5/2.5 | 95.5 | 10290 | 47.83 |
| F4 5/5/5/5 | 66.7 | 4335 | 5.46 |
| Mencevax ™ | 85.7 | 8022 | 27.39 |

| Formulation | % SBA MenC responders | SBA-MenC GMT | Anti-PSC CMC µg/ml ELISA |
|---|---|---|---|
| F 1 5AH/5/5/5 | 69.6 | 3989 | 12.11 |
| F2 2.5AH/5/2.5/2.5 | 81.8 | 3524 | 12.78 |
| F3 5AH/5/2.5/2.5 | 81.8 | 3608 | 8.4 |
| F4 5/5/5/5 | 73.9 | 2391 | 8.84 |
| Mencevax ™ | 90.0 | 5447 | 38.71 |

| | % SBA MenW | SBA-MenW | Anti-PSW CMC µg/ml ELISA |
|---|---|---|---|
| F 1 5AH/5/5/5 | 95 | 5418 | 9.65 |
| F2 2.5AH/5/2.5/2.5 | 85 | 4469 | 14.55 |
| F3 5AH/5/2.5/2.5 | 95.5 | 4257 | 6.39 |
| F4 5/5/5/5 | 95.5 | 4621 | 10.7 |
| Mencevax ™ | 86.4 | 2714 | 13.57 |

| Formulation | % SBY MenY responders | SBA-MenY GMT | Anti-PSY CMC µg/ml ELISA |
|---|---|---|---|
| F 1 5AH/5/5/5 | 91.3 | 7122 | 16.3 |
| F2 2.5AH/5/2.5/2.5 | 87.5 | 5755 | 12.52 |
| F3 5AH/5/2.5/2.5 | 80 | 5928 | 8.88 |
| F4 5/5/5/5 | 91.3 | 6742 | 13.88 |
| Mencevax ™ | 91.7 | 4854 | 21.02 |

Example 4

Clinical Trial Assessing the Effect of a Linker in MenA and MenC Conjugates in a MenACWY Conjugate Vaccine A single dose of different formulations of MenACWY vaccine was administered to teenagers of 15-19 years in 5 groups of 25 subjects in a 1:1:1:1:1 randomised trial. The formulations tested were:

F1—MenACWY conjugated to tetanus toxoid with the MenA and MenC conjugates containing an AH spacer (made according to example 1)—2.5/2.5/2.5/2.5 µg
F2—MenACWY conjugated to tetanus toxoid with the MenA and MenC conjugates containing an AH spacer (made according to example 1)—5/5/2.5/2.5n
F3—MenACWY conjugated to tetanus toxoid with the MenA and MenC conjugates containing an AH spacer (made according to example 1)—5/5/5/5 µg
F4—MenACWY conjugated to tetanus toxoid with the MenA conjugate containing an AH spacer (made according to example 1)—5/5/5/5 µg
Control group—Mencevax™ ACWY
On day 30 after inoculation, a blood sample was taken from the patients.

The blood samples were used to assess the percentage of SBA-MenA, SBA-MenC, SBA-MenW135 and SBA-MenY responders one month after the vaccine dose. A vaccine response was defined as 1) for initially seronegative subjects—a post-vaccination antibody titre$\geq$1/32 at 1 month or 2) for initially seropositive subjects—antibody titre of $\geq$4 fold the pre-vaccination antibody titre.

Results

The introduction of an AH spacer into the MenC conjugate led to an increase in the immune response against MenC as shown in the Table below. This is demonstrated by an increase in SBA GMT from 1943 to 4329 and an increase in anti-PSC GMC from 7.65 to 13.13. Good immune responses against MenA, MenW and MenY were maintained.

| Formulation | % SBA MenA responders | SBA-MenA GMT | Anti-PSA CMC µg/ml ELISA |
|---|---|---|---|
| F 1 2.5AH/2.5AH/2.5/2.5 | 75 | 8417 | 20.23 |
| F2 5AH/5AH/2.5/2.5 | 72 | 6299 | 16.07 |
| F3 5AH/5AH/5/5 | 87 | 9264 | 27.26 |
| F4 5AH/5/5/5 | 77.3 | 9632 | 20.39 |
| Mencevax ™ | 78.3 | 8284 | 12.93 |

| Formulation | % SBA MenC responders | SBA-MenC GMT | Anti-PSC CMC µg/ml ELISA |
|---|---|---|---|
| F 1 2.5AH/2.5AH/2.5/2.5 | 88 | 3619 | 12.82 |
| F2 5AH/5AH/2.5/2.5 | 88 | 2833 | 13.32 |
| F3 5AH/5AH/5/5 | 95.8 | 4329 | 13.13 |
| F4 5AH/5/5/5 | 95.8 | 1943 | 7.65 |
| Mencevax ™ | 91.7 | 1567 | 16.55 |

| Formulation | % SBA MenW responders | SBA-MenW GMT | Anti-PSW GMC µg/ml ELISA |
|---|---|---|---|
| F 1 2.5AH/2.5AH/2.5/2.5 | 100 | 5656 | 7 |
| F2 5AH/5AH/2.5/2.5 | 96 | 4679 | 5.4 |
| F3 5AH/5AH/5/5 | 91.3 | 4422 | 4.45 |
| F4 5AH/5/5/5 | 88 | 4947 | 7.67 |
| Mencevax ™ | 96 | 3486 | 11.93 |

| Formulation | % SBY MenY responders | SBA-MenY GMT | Anti-PSY GMC µg/ml ELISA |
|---|---|---|---|
| F 1 2.5AH/2.5AH/2.5/2.5 | 75 | 3891 | 17.81 |
| F2 5AH/5AH/2.5/2.5 | 92 | 3968 | 11.96 |
| F3 5AH/5AH/5/5 | 79.2 | 2756 | 9.51 |
| F4 5AH/5/5/5 | 80 | 3914 | 16.76 |
| Mencevax ™ | 88 | 3056 | 21.41 |

The invention claimed is:

1. A method of making an immunogenic composition comprising conjugating a saccharide to a protein carrier using carbodiimide condensation chemistry, wherein the saccharide comprises or has been derivatised to comprise, amino and/or carboxyl groups, and wherein the protein carrier comprises, or has been derivatised to comprise, amino and/or carboxyl groups, comprising the steps of:
I)—if the protein carrier comprises both amino and carboxyl groups and the saccharide comprises either amino or carboxyl groups:
a) mixing the saccharide and aliquot of carbodiimide required to perform the conjugation, and
b) adding the aliquot of protein carrier required over a period of 1 minute to 5 hours;

II)—if the saccharide comprises both amino and carboxyl groups and the protein carrier comprises either amino or carboxyl groups:
  a) mixing the protein carrier and aliquot of carbodiimide required to perform the conjugation, and
  b) adding the aliquot of saccharide required over a period of 35 seconds to 6 hours;

III)—if the saccharide comprises both amino and carboxyl groups and the protein carrier comprises both amino and carboxyl groups:
  a) mixing the protein carrier and saccharide, and
  b) adding the aliquot of carbodiimide required to perform the conjugation over a period of 35 seconds to 6 hours.

2. The method of claim 1, wherein in step b) the period is 1 minute to 4 hours, 2 minutes to 3 hours, 3 minutes to 2 hours, 4 to 60 minutes, 5 to 50 minutes, 6 to 40 minutes, 7 to 30 minutes or 8 to 20 minutes.

3. The method of claim 1, wherein in step b) the period is 10 minutes to 4 hours, 20 minutes to 3 hours, 30 minutes to 2 hours, 40 to 90 minutes, or 50 to 70 minutes.

4. The method of claim 1, wherein the carbodiimide is EDAC (1-ethyl-3-(3-dimethyl-aminopropyl)carbodiimide).

5. The method of claim 1, wherein the aliquot of carbodiimide required to perform the conjugation is 0.01 to 3, 0.05 to 2 or 0.09 to 1 mg/mg saccharide.

6. The method of claim 1, wherein the saccharide and/or protein carrier has been derivatised to comprise amino or carboxyl groups.

7. The method of claim 6, wherein the derivatisation is through the addition of a hetero- or homo-bifunctional linker.

8. The method of claim 7, wherein the linker has between 4 and 12 carbon atoms.

9. The method of claim 7, wherein the linker has two reactive amino groups.

10. The immunogenic composition of claim 7, wherein the linker is adipic acid dihydrazide (ADH).

11. The method of claim 7, wherein the linker has two reactive carboxylic acid groups.

12. The method of claim 7, wherein the linker has a reactive amino group at one end and a reactive carboxylic acid group at the other end.

13. The method of claim 7, wherein the derivatization takes place through reacting a large excess of linker with the saccharide and/or protein carrier to be derivatised.

14. The method of claim 7, wherein the saccharide comprises a reactive hydroxyl group as part of its repeating unit which is partially derivatised via an amino group on the linker.

15. The method of claim 14, wherein the saccharide is partially derivatised with 1-cyano-4-dimethylamino pyridinium tetrafluoroborate (CDAP) chemistry.

16. The method of claim 7, wherein the saccharide comprises a reactive amino group as part of its repeating unit which is partially derivatised via a carboxyl group on the linker.

17. The method of claim 16, wherein the saccharide is partially derivatised with carbodiimide condensation chemistry.

18. The method of claim 7, wherein the saccharide comprises a reactive carboxyl group as part of its repeating unit which is partially derivatised via an amino group on the linker.

19. The method of claim 18, wherein the saccharide is partially derivatised with carbodiimide chemistry.

20. The method of claim 1, wherein in step b) the aliquot of carbodiimide, saccharide or protein carrier is added at a constant rate using a pump.

21. The method of claim 1, wherein in step b) the aliquot of carbodiimide, saccharide or protein carrier is added in stages over the period.

22. The method of claim 21, wherein at least one quarter of the aliquot is added over the first half of the period, and at least one quarter of the aliquot over the second half of the period.

23. The method of claim 21, wherein the aliquot 'a' is added in 4-100 stages 's'.

24. The method of claim 23, wherein a/s of the aliquot is added at each stage.

25. The method of claim 23, wherein if one stage takes place at time zero of the period 'p', each subsequent stage takes place at a time which is p/(s−1).

26. The method of claim 1, wherein the saccharide is present at a final concentration of 0.5-50 mg/ml in step b).

27. The method of claim 1, wherein the initial ratio of protein carrier to saccharide is 5:1 to 1:5, 4:1 to 1:1, or 3:1 to 2:1 (w/w).

28. The method of claim 1, wherein the concentration of salt present in step b) is 0-2, 0.1-1 or 0.2-0.5 M.

29. The method of claim 1, wherein the protein carrier is present at a final concentration of 1-50 mg/ml in step b).

30. The method of claim 1, wherein the reaction pH in step b) is maintained at pH 4.5-6.5, 4.7-6.0, or 5-5.5.

31. The method of claim 1, wherein N-hydroxysuccinimide is also present in the reaction in step b), and the reaction pH in step b) is maintained at pH 4.5-7.5.

32. The method of claim 1, wherein the temperature of the reaction in step b) is maintained at 4-37, 10-32, 17-30, or 22-27° C.

33. The method of claim 1, wherein after the aliquot has all been added in step b) the reaction is maintained for a further 10 minutes to 72 hours, 20 minutes to 48 hours, 30 minutes to 24 hours, 40 minutes to 12 hours, 50 minutes to 6 hours, or 1-3 hours.

34. The method of claim 1, wherein once the reaction is completed the pH is adjusted to 7.5-9.

35. The method of claim 1, comprising a subsequent step c), wherein the saccharide-protein conjugate is purified on a size exclusion chromatography column.

36. The method of claim 35, comprising a subsequent step d), wherein the saccharide-protein conjugate is sterile filtered.

37. The method of claim 36, comprising a subsequent step e), wherein an effective dose of the saccharide-protein conjugate is formulated with a pharmaceutically acceptable excipient to manufacture an immunogenic composition or vaccine.

38. The method of claim 1, wherein the saccharide is a bacterial capsular saccharide.

39. The method of claim 1, wherein the weight-average molecular weight of the saccharide is 1000-2000000, 5000-1000000, 10000-500000, 50000-400000, 75000-300000, or 100000-200000.

40. The method of claim 1, wherein the saccharide is either a native polysaccharide or is sized by a factor of no more than ×10.

41. The method of claim 1, wherein the saccharide is a bacterial lipooligosaccharide or lipopolysaccharide.

42. The method of claim 1, wherein the protein carrier comprises one or more T-helper epitopes.

43. The method of claim 1, wherein the protein carrier is selected from the group consisting of: TT, DT, CRM197, fragment C of TT, protein D of *H. influenzae*, pneumococcal PhtD, and pneumococcal Pneumolysin.

44. The method of claim 28, wherein the salt is NaCl.

45. The method of claim 38, wherein bacterial capsular saccharide is derived from a bacterium selected from a list consisting of: *N. meningitidis* serogroup A, B, C, W135 or Y, *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20, 22F, 23F or 33F, Group B *Streptococcus* group Ia, Ib, II, III, IV, V, VI, or VII, *Staphylococcus aureus* type 5, *Staphylococcus aureus* type 8, *Salmonella typhi* (Vi saccharide), *Vibrio cholerae*, or *H. influenzae* type b.

46. The method of claim 40, wherein the saccharide is sized by microfluidization.

47. The method of claim 41, wherein the bacterial lipooligosaccharide or lipopolysaccharide is derived from a bacterium selected from a list consisting of: *N. meningitidis, H. influenzae, E. coli, Salmonella* or *M. catarrhalis*.

48. The method of claim 1, wherein in step II) b) or III) b) the period is 50 seconds to 5 hours.

49. The method of claim 1, wherein in II) b) or III) b) the period is 1 minute to 5 hours.

* * * * *